US008760508B2

(12) United States Patent
Brantley et al.

(10) Patent No.: US 8,760,508 B2
(45) Date of Patent: Jun. 24, 2014

(54) FILTERED SMOKING ARTICLE INSPECTION SYSTEM, AND ASSOCIATED METHOD

(75) Inventors: Franklin Forrest Brantley, Winston-Salem, NC (US); Eddie Lee Nuckols, Mocksville, NC (US); Darrell Thomas Dixon, Clemmons, NC (US); Timothy Frederick Thomas, High Point, NC (US); Calvin Wayne Henderson, Lewisville, NC (US); Balager Ademe, Winston-Salem, NC (US)

(73) Assignee: R.J. Reynolds Tobacco Company, Winston-Salem, NC (US)

( * ) Notice: Subject to any disclaimer, the term of this patent is extended or adjusted under 35 U.S.C. 154(b) by 484 days.

(21) Appl. No.: 12/686,489

(22) Filed: Jan. 13, 2010

(65) Prior Publication Data

US 2011/0169942 A1 Jul. 14, 2011

(51) Int. Cl.
*H04N 7/18* (2006.01)

(52) U.S. Cl.
USPC .......... 348/98; 131/280; 382/141; 356/237.2; 209/535

(58) Field of Classification Search
None
See application file for complete search history.

(56) References Cited

U.S. PATENT DOCUMENTS

| | | | |
|---|---|---|---|
| 3,288,147 A | 11/1966 | Molins et al. | |
| 3,301,454 A | 1/1967 | Wayne et al. | |
| 3,308,600 A | 3/1967 | Erdmann et al. | |
| 3,366,121 A | 1/1968 | Carty | |
| 3,398,675 A | 8/1968 | Potter et al. | |
| 3,424,172 A | 1/1969 | Neurath | |
| 3,428,049 A | 2/1969 | Leake et al. | |
| 3,444,517 A | 5/1969 | Rabinow | |
| 3,550,508 A | 12/1970 | Wartman, Jr. | |
| 3,550,598 A | 12/1970 | McGlumphy et al. | |

(Continued)

FOREIGN PATENT DOCUMENTS

CN 1276999 12/2000
CN 1468068 1/2004

(Continued)

OTHER PUBLICATIONS

Johnson "Development of Cigarette Components to Meet Industry Needs," 52$^{nd}$ T.S.R.C., Sep. 1998.

(Continued)

*Primary Examiner* — Behrooz Senfi
*Assistant Examiner* — Mohammed Jebari
(74) *Attorney, Agent, or Firm* — Womble Carlyle Sandridge & Rice, LLP

(57) ABSTRACT

An inspection system and associated method are provided for inspecting a smoking article having a smokable rod and a filter element serially secured together by a tipping material circumscribing a longitudinal periphery of the filter element and a portion of a longitudinal periphery of the smokable rod adjacent to the filter element. A transport device is configured to transport individual as-formed smoking articles from a first to a second position such that the tipping material associated with each smoking article is accessible at least about the portion of the longitudinal periphery of the smoking article. An inspection device is configured to optically inspect each smoking article, at least about the portion of the longitudinal periphery of the smoking article having the tipping material, as the smoking article is transported between the first and second positions, and to automatically determine from the optical inspection whether the inspected smoking article is defective.

26 Claims, 6 Drawing Sheets

(56) References Cited

U.S. PATENT DOCUMENTS

| | | | |
|---|---|---|---|
| 3,575,276 A * | 4/1971 | Rupert | 198/457.01 |
| 3,602,231 A | 8/1971 | Dock | |
| 3,685,521 A | 8/1972 | Dock | |
| 3,818,223 A | 6/1974 | Gibson et al. | |
| 3,884,246 A | 5/1975 | Walker | |
| 3,915,176 A | 10/1975 | Heitmann et al. | |
| 4,053,056 A | 10/1977 | Day | |
| 4,083,460 A * | 4/1978 | Venturi | 414/791.6 |
| 4,171,739 A | 10/1979 | Yamato | |
| 4,174,719 A | 11/1979 | Martin et al. | |
| 4,238,993 A | 12/1980 | Brand et al. | |
| 4,280,187 A | 7/1981 | Reuland et al. | |
| 4,281,670 A | 8/1981 | Heitmann et al. | |
| 4,281,671 A | 8/1981 | Byrne et al. | |
| 4,284,088 A | 8/1981 | Brand et al. | |
| 4,291,713 A | 9/1981 | Frank | |
| 4,294,353 A | 10/1981 | Focke et al. | |
| RE30,964 E | 6/1982 | Butner et al. | |
| 4,403,620 A | 9/1983 | Joseph et al. | |
| 4,445,520 A | 5/1984 | Knight et al. | |
| 4,474,190 A | 10/1984 | Brand | |
| 4,534,463 A | 8/1985 | Bouchard | |
| 4,574,816 A | 3/1986 | Rudszinat | |
| 4,715,497 A | 12/1987 | Focke et al. | |
| 4,736,754 A | 4/1988 | Heitmann et al. | |
| 4,781,203 A | 11/1988 | La Hue | |
| 4,807,809 A | 2/1989 | Pryor et al. | |
| 4,811,745 A | 3/1989 | Cohen et al. | |
| 4,844,100 A | 7/1989 | Holznagel | |
| 4,850,301 A | 7/1989 | Greene, Jr. et al. | |
| 4,852,734 A | 8/1989 | Allen et al. | |
| 4,862,905 A | 9/1989 | Green, Jr. et al. | |
| 4,878,506 A | 11/1989 | Pinck et al. | |
| 4,889,144 A | 12/1989 | Tateno et al. | |
| 4,920,990 A | 5/1990 | Lawrence et al. | |
| 4,925,602 A | 5/1990 | Hill et al. | |
| 5,012,823 A | 5/1991 | Keritsis et al. | |
| 5,012,829 A | 5/1991 | Thesing et al. | |
| 5,025,814 A | 6/1991 | Raker | |
| 5,060,664 A | 10/1991 | Siems et al. | |
| 5,060,665 A | 10/1991 | Heitmann | |
| 5,074,320 A | 12/1991 | Jones, Jr. et al. | |
| 5,101,609 A | 4/1992 | Cook | |
| 5,101,839 A | 4/1992 | Jakob et al. | |
| 5,105,838 A | 4/1992 | White et al. | |
| 5,131,416 A | 7/1992 | Gentry | |
| 5,139,140 A | 8/1992 | Burrows et al. | |
| 5,156,169 A | 10/1992 | Holmes et al. | |
| 5,159,944 A | 11/1992 | Arzonico et al. | |
| 5,167,244 A | 12/1992 | Kjerstad | |
| 5,191,906 A | 3/1993 | Myracle, Jr. | |
| 5,220,930 A | 6/1993 | Gentry | |
| 5,225,277 A | 7/1993 | Takegawa et al. | |
| 5,240,117 A | 8/1993 | Focke et al. | |
| 5,271,419 A | 12/1993 | Arzonico et al. | |
| 5,333,729 A | 8/1994 | Wolfe | |
| 5,353,357 A * | 10/1994 | Longest et al. | 382/141 |
| 5,360,023 A | 11/1994 | Blakeley et al. | |
| 5,387,285 A | 2/1995 | Rivers | |
| 5,396,909 A | 3/1995 | Gentry et al. | |
| 5,432,600 A * | 7/1995 | Grollimund et al. | 356/237.2 |
| 5,472,002 A | 12/1995 | Covarrubias | |
| 5,476,108 A | 12/1995 | Dominguez et al. | |
| 5,515,159 A | 5/1996 | Sites et al. | |
| 5,588,068 A | 12/1996 | Longest et al. | |
| 5,660,382 A | 8/1997 | Meier | |
| 5,718,250 A | 2/1998 | Banerjee et al. | |
| 5,740,902 A | 4/1998 | Spatafora | |
| 5,898,104 A | 4/1999 | Rohrssen et al. | |
| 5,938,018 A | 8/1999 | Keaveney et al. | |
| 5,977,780 A | 11/1999 | Herrmann | |
| 6,020,969 A | 2/2000 | Struckhoff et al. | |
| 6,054,665 A | 4/2000 | Focke et al. | |
| 6,117,455 A | 9/2000 | Takada et al. | |
| 6,158,193 A | 12/2000 | Focke et al. | |
| 6,213,128 B1 * | 4/2001 | Smith et al. | 131/280 |
| 6,229,115 B1 | 5/2001 | Vos et al. | |
| 6,246,778 B1 | 6/2001 | Moore | |
| 6,360,751 B1 | 3/2002 | Fagg et al. | |
| 6,384,359 B1 | 5/2002 | Belcastro et al. | |
| 6,385,333 B1 | 5/2002 | Puckett et al. | |
| 6,437,317 B1 | 8/2002 | Focke et al. | |
| 6,537,186 B1 | 3/2003 | Veluz | |
| 6,612,429 B2 | 9/2003 | Dennen | |
| 6,647,878 B2 | 11/2003 | Blau et al. | |
| 6,726,006 B1 | 4/2004 | Funderburk et al. | |
| 6,736,261 B1 | 5/2004 | Thomas et al. | |
| 6,761,174 B2 | 7/2004 | Jupe et al. | |
| 6,779,530 B2 | 8/2004 | Kraker | |
| 6,813,961 B2 | 11/2004 | Stiller et al. | |
| 6,848,449 B2 | 2/2005 | Kitao et al. | |
| 6,904,917 B2 | 6/2005 | Kitao et al. | |
| 7,074,170 B2 | 7/2006 | Lanier, Jr. et al. | |
| 7,115,085 B2 | 10/2006 | Deal | |
| 7,210,486 B2 | 5/2007 | Hartmann | |
| 7,234,271 B1 | 6/2007 | Fitzgerald et al. | |
| 7,237,559 B2 | 7/2007 | Ashcraft et al. | |
| 7,240,678 B2 | 7/2007 | Crooks et al. | |
| 7,275,548 B2 | 10/2007 | Hancock et al. | |
| 7,281,540 B2 | 10/2007 | Barnes et al. | |
| 7,296,578 B2 | 11/2007 | Read, Jr. | |
| 7,325,382 B2 | 2/2008 | Nelson et al. | |
| 7,434,585 B2 | 10/2008 | Holmes | |
| 7,479,098 B2 | 1/2009 | Thomas et al. | |
| 7,565,818 B2 | 7/2009 | Thomas et al. | |
| 7,578,298 B2 | 8/2009 | Karles et al. | |
| 7,654,945 B2 | 2/2010 | Deal | |
| 7,740,019 B2 | 6/2010 | Nelson et al. | |
| 7,744,922 B2 | 6/2010 | Mane et al. | |
| 7,784,356 B2 * | 8/2010 | Spiers et al. | 73/856 |
| 7,833,146 B2 | 11/2010 | Deal | |
| 7,836,895 B2 | 11/2010 | Dube et al. | |
| 7,861,728 B2 | 1/2011 | Holton, Jr. et al. | |
| 7,972,254 B2 | 7/2011 | Stokes et al. | |
| 8,142,339 B2 | 3/2012 | Deal | |
| 8,186,359 B2 | 5/2012 | Ademe et al. | |
| 8,262,550 B2 | 9/2012 | Barnes et al. | |
| 8,308,623 B2 | 11/2012 | Nelson et al. | |
| 2001/0032932 A1 | 10/2001 | Focke | |
| 2002/0185141 A1 | 12/2002 | Heide | |
| 2003/0136419 A1 | 7/2003 | Muller | |
| 2003/0137312 A1 | 7/2003 | Cerati et al. | |
| 2003/0145866 A1 | 8/2003 | Hartmann | |
| 2003/0178036 A1 | 9/2003 | Demmer et al. | |
| 2003/0206023 A1 | 11/2003 | Herrmann | |
| 2004/0129281 A1 | 7/2004 | Hancock et al. | |
| 2004/0141174 A1 | 7/2004 | Focke et al. | |
| 2004/0217023 A1 | 11/2004 | Fagg et al. | |
| 2004/0256253 A1 | 12/2004 | Henson et al. | |
| 2004/0261807 A1 | 12/2004 | Dube et al. | |
| 2005/0016556 A1 | 1/2005 | Ashcraft et al. | |
| 2005/0039764 A1 | 2/2005 | Barnes et al. | |
| 2005/0066986 A1 | 3/2005 | Nestor et al. | |
| 2005/0075754 A1 | 4/2005 | Zeitler et al. | |
| 2005/0076929 A1 | 4/2005 | Fitzgerald et al. | |
| 2005/0112228 A1 | 5/2005 | Smith et al. | |
| 2005/0150786 A1 | 7/2005 | Mitten et al. | |
| 2006/0169295 A1 | 8/2006 | Draghetti | |
| 2006/0207616 A1 | 9/2006 | Hapke et al. | |
| 2006/0243611 A1 | 11/2006 | Wu | |
| 2006/0272655 A1 | 12/2006 | Thomas et al. | |
| 2007/0056600 A1 | 3/2007 | Coleman, III et al. | |
| 2007/0091326 A1 | 4/2007 | Schroeder et al. | |
| 2007/0102015 A1 | 5/2007 | Villarinho | |
| 2007/0144542 A1 | 6/2007 | Bencivenni et al. | |
| 2007/0215167 A1 | 9/2007 | Crooks et al. | |
| 2007/0246055 A1 | 10/2007 | Oglesby | |
| 2008/0029118 A1 | 2/2008 | Nelson et al. | |
| 2008/0093234 A1 | 4/2008 | Jones et al. | |
| 2008/0099353 A1 | 5/2008 | Parsons et al. | |
| 2008/0142028 A1 | 6/2008 | Fagg | |
| 2008/0179204 A1 | 7/2008 | Lutzig | |
| 2008/0202540 A1 | 8/2008 | Carter et al. | |
| 2009/0050163 A1 | 2/2009 | Hartmannn et al. | |

(56) References Cited

U.S. PATENT DOCUMENTS

| | | | |
|---|---|---|---|
| 2009/0066948 A1 | 3/2009 | Karpowicz et al. | |
| 2009/0090372 A1 | 4/2009 | Thomas et al. | |
| 2009/0120449 A1 | 5/2009 | Tindall | |
| 2009/0194118 A1 | 8/2009 | Ademe et al. | |
| 2010/0059074 A1* | 3/2010 | Brantley et al. | 131/280 |
| 2010/0101589 A1 | 4/2010 | Nelson et al. | |
| 2010/0184576 A1 | 7/2010 | Prestia et al. | |
| 2010/0236561 A1 | 9/2010 | Barnes et al. | |
| 2010/0293106 A1 | 11/2010 | Rhoads et al. | |
| 2010/0294290 A1 | 11/2010 | Zhang | |
| 2011/0053745 A1 | 3/2011 | Iliev et al. | |
| 2011/0067976 A1 | 3/2011 | Pelagatti | |
| 2011/0162662 A1 | 7/2011 | Nikolov et al. | |
| 2011/0162665 A1 | 7/2011 | Burov et al. | |
| 2011/0169942 A1 | 7/2011 | Brantley et al. | |
| 2011/0230320 A1 | 9/2011 | Stokes et al. | |
| 2011/0271968 A1 | 11/2011 | Carpenter et al. | |
| 2012/0037546 A1 | 2/2012 | Dixon et al. | |
| 2012/0055493 A1 | 3/2012 | Novak, III et al. | |
| 2012/0077658 A1 | 3/2012 | Nikolov et al. | |
| 2012/0080043 A1 | 4/2012 | Naenen et al. | |
| 2012/0120229 A1 | 5/2012 | Brantley et al. | |
| 2012/0245006 A1 | 9/2012 | Henley et al. | |
| 2012/0245007 A1 | 9/2012 | Henley et al. | |
| 2013/0085052 A1 | 4/2013 | Novak, III et al. | |
| 2013/0096711 A1 | 4/2013 | Gates et al. | |

FOREIGN PATENT DOCUMENTS

| | | |
|---|---|---|
| CN | 1642724 | 7/2005 |
| CN | 1939165 | 4/2007 |
| CN | 101257809 | 9/2008 |
| DE | 10238906 | 3/2004 |
| DE | 10 2008 062 370 | 6/2010 |
| EP | 0 292 949 A2 | 11/1988 |
| EP | 0 704 172 | 4/1996 |
| EP | 1 669 755 | 6/2006 |
| EP | 1 754 419 A1 | 2/2007 |
| EP | 1 767 107 | 3/2007 |
| EP | 1 916 188 | 4/2008 |
| EP | 2 243 384 A1 | 10/2010 |
| GB | 1058343 A2 | 2/1967 |
| GB | 2 020 158 | 11/1979 |
| GB | 1042000 | 9/1996 |
| JP | 9325123 | 12/1997 |
| JP | 2001-190262 | 7/2001 |
| JP | 2003-219855 | 8/2003 |
| JP | 2004-504825 | 2/2004 |
| WO | WO 01/79092 | 10/2001 |
| WO | WO 03/009711 | 2/2003 |
| WO | WO 03/047836 | 6/2003 |
| WO | WO 03/082558 | 10/2003 |
| WO | WO 2005/113386 | 12/2005 |
| WO | WO 2006/064371 | 6/2006 |
| WO | WO 2006/092962 | 9/2006 |
| WO | WO 2007/028957 | 3/2007 |
| WO | WO 2007/038053 | 4/2007 |
| WO | WO 2013/145163 | 10/2013 |

OTHER PUBLICATIONS

Davis et al., *Tobacco Production, Chemistry and Technology*, 1999, pp. 440-460. Blackwell Science, Inc., Malden, MA.

* cited by examiner

FILTERED SMOKING ARTICLE INSPECTION SYSTEM, AND ASSOCIATED METHOD

BACKGROUND OF THE DISCLOSURE

1. Field of the Disclosure

The present disclosure relates to smoking articles, such as filtered cigarettes, and, more particularly, to a filtered smoking article inspection system and associated method.

2. Description of Related Art

Popular smoking articles, such as cigarettes, have a substantially cylindrical rod shaped structure and include a charge, roll, or column of smokable material such as shredded tobacco (e.g., in cut filler form) surrounded by a paper wrapper thereby forming a so-called "smokable rod" or "tobacco rod." Normally, a cigarette has a cylindrical filter element aligned in an end-to-end relationship with the tobacco rod. Typically, a filter element comprises cellulose acetate tow plasticized using triacetin, and the tow is circumscribed by a paper material known as "plug wrap." A cigarette can incorporate a filter element having multiple segments, and one of those segments can comprise activated charcoal particles. See, for example, U.S. Pat. No. 6,537,186 to Veluz; PCT Publication No. WO 2006/064371 to Banerjea; and U.S. Patent Application Publication No. US 2007/0056600 to Coleman III, et al.; each of which is incorporated herein by reference. Typically, the filter element is attached to one end of the tobacco rod using a circumscribing wrapping material known as "tipping paper," in order to provide a so-called "filtered cigarette." It also has become desirable to perforate the tipping material and plug wrap, in order to provide dilution of drawn mainstream smoke with ambient air. Descriptions of cigarettes and the various components thereof are set forth *Tobacco Production, Chemistry and Technology*, Davis et al. (Eds.) (1999). A cigarette is employed by a smoker by lighting the lighting end terminus thereof opposite the filter element and burning the tobacco rod. The smoker then receives mainstream smoke into his/her mouth by drawing on the opposite end (e.g., the filter element or mouth end terminus) of the cigarette.

More particularly, the filter element may be attached to the tobacco rod using tipping material (e.g., essentially air impermeable tipping paper), that circumscribes both the entire length of the filter element and an adjacent region of the tobacco rod. The inner surface of the tipping material is fixedly secured to the outer surface of the plug wrap circumscribing the filter tow and the outer surface of the wrapping material/paper wrapper surrounding the smokable material of the tobacco rod, using a suitable adhesive; and hence, the filter element and the tobacco rod are connected to one another. The adhesive may also function to secure the overlapping ends of the tipping material circumscribing the filter element and tobacco rod.

A ventilated or air diluted smoking article can be provided with an optional air dilution provisions, such as a series of perforations, each of which extend through the tipping material and plug wrap. The optional perforations can be made by various techniques known to those of ordinary skill in the art, such as laser perforation techniques. Otherwise, so-called off-line air dilution techniques can be used (e.g., through the use of porous paper plug wrap and pre-perforated tipping paper). For cigarettes that are air diluted or ventilated, the amount or degree of air dilution or ventilation can vary. Frequently, the amount of air dilution for an air diluted cigarette is greater than about 10 percent, generally is greater than about 20 percent, often is greater than about 30 percent, and sometimes is greater than about 40 percent. Typically, the upper level for air dilution for an air diluted cigarette is less than about 80 percent, and often is less than about 70 percent. As used herein, the term "air dilution" is the ratio (expressed as a percentage) of the volume of air drawn through the air dilution provisions to the total volume and air and smoke drawn through the cigarette and exiting the extreme mouth end portion of the cigarette.

The dimensions of a representative filtered cigarette can vary. Preferred cigarettes are rod-shaped, and can have diameters of about 7.5 mm (e.g., circumferences of about 20 mm to about 27 mm, often about 22.5 mm to about 25 mm); and can have total lengths of about 70 mm to about 120 mm, often about 80 mm to about 100 mm. The length of the filter element can vary. Typical filter elements can have total lengths of about 15 mm to about 40 mm, often about 20 mm to about 35 mm. For a typical dual-segment filter element, the downstream or mouth end filter segment often has a length of about 10 mm to about 20 mm; and the upstream or tobacco rod end filter segment often has a length of about 10 mm to about 20 mm.

However, in the manufacture of filtered smoking articles, such as filtered cigarettes, the procedure for securing the filter element to the tobacco rod during the tipping process or for forming the tobacco rod itself (i.e., wrapping a smokable material with an outer circumscribing layer of a wrapping material) may result in certain undesirable defects in the smoking article formed thereby. For example, the tipping material may be misaligned with respect to the smoking article (i.e., forming a spiral instead of a cylinder when wrapped about the smoking article), the wrapping material may be misaligned with respect to the smokable material, the tipping material or the wrapping material may be wrinkled, the tipping material or the wrapping material may be visibly contaminated (i.e., spots or other undesirable discolorations or stains), the wrong tipping material may be used (i.e., the actual tipping material may not correspond to the specified material), the wrong wrapping material may be used, multiple units of the tipping material may be applied to the smoking article (i.e., units of the tipping paper, in excess of the specified amount, may get stuck together and applied about the smoking article), multiple units of the wrapping material may be applied to the smokable material, the adhesive securing the tipping material may not be evenly applied about the smoking article or the tipping material may be inconsistently adhered to the smoking article (or the overlapping ends of the tipping paper may not be securely adhered together), the overlapping ends of the wrapping material may not be securely adhered together (thus exposing the smokable material), the tipping material may be rolled over itself along the portion of the longitudinal periphery of the smokable rod (i.e., forming a raised "collar" about the smoking article), the tipping material may not completely secure the tobacco rod to the filter element (i.e., the tobacco rod may not be secured to and may thus easily separate from the filter element), the tipping material may not extend at least along the portion of the longitudinal periphery of the smokable rod, as specified, the wrapping material may have been punctured (i.e., torn, pulled, or had a hole formed therein, for instance, by stem portions in the tobacco material comprising the smokable material) to expose the smokable material, and (excess) adhesive securing one of the tipping material about the smoking article and the wrapping material about the smokable material may be exposed.

It follows that, due to the high speed nature of the cigarette manufacturing process, many of the defects that may occur during the tipping process may not be readily apparent or otherwise detected before the product is packaged for sale. As such, it may often be the smoker (end user) opening the pack of cigarettes discovering any defects in individual cigarettes. Such a situation is generally undesirable to the perception of the quality of the product. As such, there exists a need for a method and system for inspecting individual smoking articles, such as filtered cigarettes, for defects prior to the products being packaged for distribution and sale. In some instances, such an apparatus and method may desirably be used to halt or pause the production process upon detection of certain defects, amount of defects, and/or frequency of defects, such that the cause of the defects can be expediently addressed. It may also be desirable for such a solution to be readily implemented with respect to existing cigarette production machinery.

SUMMARY OF THE DISCLOSURE

The above and other needs are met by aspects of the present disclosure which, in one aspect, provides a filtered smoking article inspection system for a smoking article comprising a filter element having a mouth end terminus and a smokable rod having a lighting end terminus opposite from the filter element, wherein the smokable rod includes a smokable material having a circumscribing outer layer of a wrapping material, and wherein the smokable rod and filter element are serially secured to each other by a tipping material circumscribing the filter element along a longitudinal periphery thereof and the smokable rod along a portion of a longitudinal periphery thereof adjacent to the filter element. Such an inspection system comprises a transport device configured to transport individual as-formed smoking articles from a first position to a second position such that the tipping material associated with each smoking article is accessible at least about the portion of the longitudinal periphery of the smoking article. An inspection device is operably engaged with the transport device and is configured to optically inspect each smoking article, at least about the portion of the longitudinal periphery of the smoking article having the tipping material, as the smoking article is transported between the first and second positions. The inspection device is further configured to automatically determine from the optical inspection whether the inspected smoking article is defective.

In another aspect, the transport device may be configured to engage the mouth end terminus of the filter element of the smoking article such that the smoking article is supported by at least the mouth end terminus between the first and second positions. In yet another aspect, the transport device may be configured to engage the lighting end terminus of the smokable rod of the smoking article such that the smoking article is supported by at least the lighting end terminus between the first and second positions. In some instances, a rotation device may be operably engaged with the transport device, with the rotation device being configured to rotate the smoking article about a longitudinal axis thereof, so as to allow the inspection device to inspect the smoking article at least about the portion of the longitudinal periphery of the smoking article having the tipping material.

In order to accomplish the optical inspection, an imaging device may be configured to capture at least one image of each smoking article, at least about the portion of the longitudinal periphery of the smoking article having the tipping material, as the smoking article is transported between the first and second positions. In some instances, a display terminal may be operably engaged with the imaging device and configured to display the at least one image of each smoking article. In other instances, the inspection device may further comprise a computer device configured to automatically process the at least one image from the imaging device to determine whether the inspected smoking article is defective.

According to another aspect a selection device may be operably engaged with the transport device, with the selection device being responsive to the inspection device to remove any smoking article determined to be defective by the inspection device. In this regard, the inspection device may be further configured to determine whether a defect exists in the smoking articles from the optical inspection thereof, with the defect being determined, for example, according to whether the tipping material is misaligned with respect to the smoking article, whether the wrapping material is misaligned with respect to the smokable material, whether one of the tipping material and the wrapping material is wrinkled, whether one of the tipping material and the wrapping material is visibly contaminated, whether one of the tipping material and the wrapping material corresponds to a specified material, whether multiple units of the tipping material have been applied to the smoking article, whether multiple units of the wrapping material have been applied to the smokable material, whether the tipping material is adhered as specified about the smoking article, whether the wrapping material is adhered as specified about the smokable material, whether the tipping material is rolled over itself along the portion of the longitudinal periphery of the smoking article, whether the tobacco rod is secured to the filter element by the tipping material, whether the tipping material extends at least along the portion of the longitudinal periphery of the smokable rod as specified, whether the wrapping material has been punctured to expose the smokable material, and whether adhesive securing one of the tipping material about the smoking article and the wrapping material about the smokable material is exposed.

According to yet another aspect, the inspection device may be configured to determine, from the optical inspection of each smoking article, whether the smoking article corresponds to a non-defective smoking article. In such instances, for example, any smoking article not corresponding to a non-defective smoking article, through the optical inspection, may be determined to be defective.

In one aspect, the transport device includes a rotatable cylinder configured to retain an individual smoking article about an outer surface thereof as the smoking article is transported between the first and second positions, wherein the inspection device may further comprise an imaging device disposed adjacent to the rotatable cylinder, and wherein the imaging device may be configured to optically inspect each smoking article at least about the portion of the longitudinal periphery of the smoking article having the tipping material as the smokable rod is transported therepast upon rotation of the cylinder.

Yet another aspect of the present disclosure comprises a method of inspecting a smoking article comprising a filter element having a mouth end terminus and a smokable rod having a lighting end terminus opposite from the filter element, wherein the smokable rod includes a smokable material having a circumscribing outer layer of a wrapping material, and wherein the smokable rod and filter element are serially secured to each other by a tipping material circumscribing the filter element along a longitudinal periphery thereof and the smokable rod along a portion of a longitudinal periphery thereof adjacent to the filter element. Such a method comprises transporting individual as-formed smoking articles from a first position to a second position with a transport device such that the tipping material associated with each smoking article is accessible at least about the portion of the longitudinal periphery of the smoking article. Each smoking article is then optically inspected with an inspection device, at least about the portion of the longitudinal periphery of the smoking article having the tipping material, as the smoking article is transported between the first and second positions, and the inspection device is configured to automatically determine whether the inspected smoking article is defective from the optical inspection thereof.

In some instances, such a method may further comprise engaging the mouth end terminus of the filter element of the smoking article with the transport device such that the smoking article is supported by the mouth end terminus between the first and second positions. In another instance, such a method may further comprise engaging the lighting end terminus of the smokable rod of the smoking article with the transport device such that the smoking article is supported by the lighting end terminus between the first and second positions. Further, in some instances, the smoking article may be rotated about a longitudinal axis thereof, with a rotation device operably engaged with the transport device, so as to allow the inspection device to inspect the smoking article at least about the portion of the longitudinal periphery of the smoking article having the tipping material. In other instances, at least one image of each smoking article may be captured with an imaging device, at least about the portion of the longitudinal periphery of the smoking article having the tipping material, as the smoking article is transported between the first and second positions.

In one aspect, such a method may further comprise displaying the at least one image of each smoking article on a display terminal operably engaged with the imaging device. In another aspect, such a method may further comprise automatically processing at least one image from the imaging device with a computer device to determine whether the inspected smoking article is defective. In still another aspect, any smoking article determined to be defective may be removed with a selection device operably engaged with the transport device, in response to the determination by the inspection device. In this regard, determining whether a defect exists in the smoking articles from the optical inspection thereof may be determined according to, for example, whether the tipping material is misaligned with respect to the smoking article, whether the wrapping material is misaligned with respect to the smokable material, whether one of the tipping material and the wrapping material is wrinkled, whether one of the tipping material and the wrapping material is visibly contaminated, whether one of the tipping material and the wrapping material corresponds to a specified material, whether multiple units of the tipping material have been applied to the smoking article, whether multiple units of the wrapping material have been applied to the smokable material, whether the tipping material is adhered as specified about the smoking article, whether the wrapping material is adhered as specified about the smokable material, whether the tipping material is rolled over itself along the portion of the longitudinal periphery of the smoking article, whether the tobacco rod is secured to the filter element by the tipping material, whether the tipping material extends at least along the portion of the longitudinal periphery of the smokable rod as specified, whether the wrapping material has been punctured to expose the smokable material, and whether adhesive securing one of the tipping material about the smoking article and the wrapping material about the smokable material is exposed.

In yet another aspect, such a method may further comprise determining, from the optical inspection of each smoking article, whether the smoking article corresponds to a non-defective smoking article. In such instances, for example, any smoking article not determined to correspond to a non-defective smoking article, through the optical inspection, may thus be determined to be defective.

In one instance, the transport device may include a rotatable cylinder, and the method may further comprise retaining an individual smoking article about an outer surface of the rotatable cylinder as the smoking article is transported between the first and second positions. In such instances, the inspection device may further comprise an imaging device disposed adjacent to the rotatable cylinder, and the method may further comprise optically inspecting each smoking article with the imaging device, at least about the portion of the longitudinal periphery of the smoking article having the tipping material, as the smoking article is transported therepast upon rotation of the cylinder Aspects of the present disclosure are thus capable of inspecting individual smoking articles, such as filtered cigarettes, for defects prior to the products being packaged for distribution and sale. In some instances, aspects of the present disclosure may also be used to halt or pause the production process upon detection of certain defects, amount of defects, and/or frequency of defects, such that the cause of the defects can be expediently addressed. Aspects of the present disclosure may also be readily implemented with respect to existing cigarette production machinery. As such, aspects of the present disclosure may be implemented to improve the physical integrity and/or aesthetic qualities of the formed cigarettes. Aspects of the present disclosure thus address the above needs and provide these and other advantages as otherwise detailed herein.

BRIEF DESCRIPTION OF THE DRAWINGS

In order to assist the understanding of aspects of the disclosure, reference will now be made to the appended drawings, which are not necessarily drawn to scale and in which like reference numerals refer to like elements. The drawings are exemplary only, and should not be construed as limiting the disclosure. For the various figures, in order to clearly show the configurations of the various wrapping materials, the thicknesses of those wrapping materials of the various filtered cigarettes may be exaggerated. Most preferably, the wrapping materials are tightly wrapped around the filtered cigarettes to provide a tight or snug fit, to provide a cigarette having acceptable physical integrity, and to provide an aesthetically pleasing appearance.

DETAILED DESCRIPTION OF THE ASPECTS OF THE DISCLOSURE

The present disclosure now will be described more fully hereinafter with reference to the accompanying drawing. The disclosure may be embodied in many different forms and should not be construed as limited to the aspects set forth herein; rather, these aspects are provided so that this disclosure will satisfy applicable legal requirements.

Figure 1:
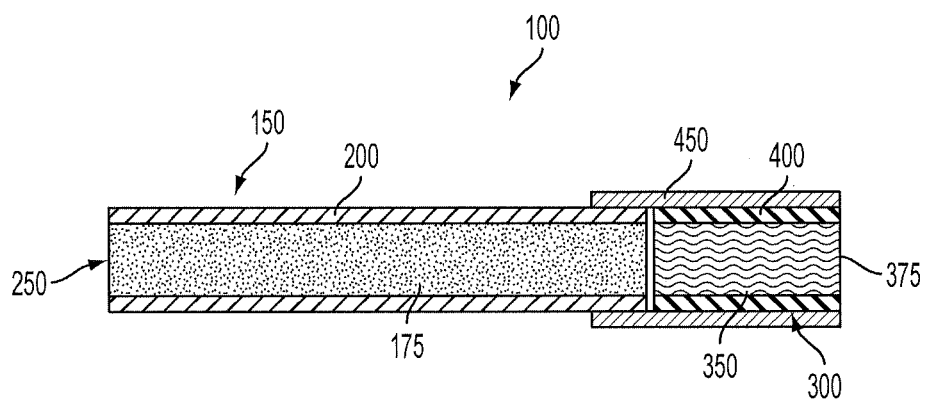
FIG. 1 is a schematic cross-sectional view of an exemplary filtered smoking article, such as a cigarette.

Referring to FIG. 1, there are shown components of a smoking article 100 in the form of a filtered cigarette. The cigarette 100 includes a generally cylindrical rod 150 of a charge or roll of smokable filler material 175 contained in a circumscribing wrapping material 200. The rod 150 is conventionally referred to as a "smokable rod" or "tobacco rod". The ends of the tobacco rod are open to expose the smokable filler material. At one end of the tobacco rod 150 is the lighting end 250 (or "lighting end terminus"), and at the other end is shown a filter element 300.

The cigarette 100 normally includes a filter element 300 or other suitable mouthpiece positioned adjacent one end of the tobacco rod 150 such that the filter element and tobacco rod are axially aligned in an end-to-end relationship, preferably abutting one another. Filter element 300 has a generally cylindrical shape, and the diameter thereof is essentially equal to the diameter of the tobacco rod. The ends of the filter element are open to permit the passage of air and smoke therethrough. The filter element 300 includes filter material 350 (e.g., plasticized cellulose acetate tow) that is overwrapped along the longitudinally extending surface thereof with circumscribing plug wrap material 400. The filter element 300 can comprise two or more filter segments (not shown), and/or flavor additives incorporated therein.

The filter element 300 is attached to the tobacco rod 150 by a tipping material 450 which circumscribes both the entire length of the filter element and an adjacent region of the tobacco rod. Opposite to the tobacco rod 150, the filter element 300 includes a mouth end 375 (or "mouth end terminus"). The inner surface of the tipping material 450 is fixedly secured to the outer surface of the plug wrap 400 and the outer surface of the wrapping material 200 of the tobacco rod, using a suitable adhesive (e.g., a water-based adhesive of the type traditionally employed by cigarette manufacturers for application of tipping paper during filtered cigarette manufacture). That is, the tipping material extends around the longitudinally extending periphery of substantially the entire length of the plug wrap, and a portion of the longitudinally extending periphery of the wrapping material of the tobacco rod in a region of the tobacco rod immediately adjacent to the filter element. Optionally, a ventilated or air-diluted smoking article is provided with air dilution provisions, such as a plurality or series of perforations (not shown), each of which extend through the tipping material 450 and plug wrap 400. Adhesive may also be applied to a longitudinally extending seam line or lap zone (not shown) of the tipping material, such as is conventionally employed during cigarette manufacture.

In some instances, the cigarette 100 may also possess one or more additional layers of tipping material (not shown) overlying and circumscribing the inner layer of tipping material 450. All or selected portions of the inner surface of the additional tipping material can be fixedly secured to the outer surface of the inner tipping material 450. As such, in some aspects, the additional tipping material may overlie the entire length of the filter element and the adjacent region of the tobacco rod. In one aspect, both tipping materials may extend essentially equal distances along the region of the tobacco rod that is adjacent the filter element. For certain cigarettes, the inner and outer tipping materials may be substantially identical in overall dimension (e.g., those tipping materials have comparable thicknesses, widths, and lengths). Optionally, a ventilated or air-diluted smoking article may be provided with air dilution provisions, such as a series of perforations, each of which extends through the outer tipping material, the inner tipping material 450, and the plug wrap 400. Adhesive can be applied to each of the tipping materials using techniques generally similar to those employed conventionally for tipping material application during cigarette manufacture.

Figure 2:
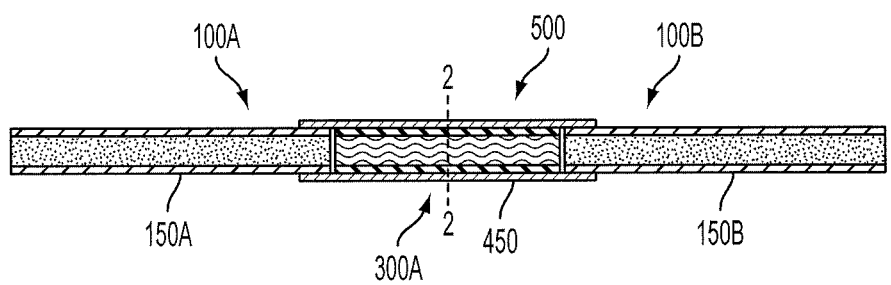
FIG. 2 is a schematic cross-sectional view of an exemplary "two-up" filtered cigarette assembly.

Referring to FIG. 2, there is shown a representative "two-up" cigarette 500 that can be subdivided along hashed line 2-2 in order to provide two filtered cigarettes 100A, 100B. In addition, representative manners or methods for providing preferred types of cigarettes are described with reference to FIG. 2. A "two-up" filter segment 300A is provided. That representative filter segment 300A possesses filter material circumscribed by plug wrap, as in FIG. 1. Two tobacco rods 150A, 150B are aligned at each end of the "two-up" filter segment 300A. A layer of tipping material 450 (e.g., a so-called "patch" of tipping material) is wrapped around the aligned components, such that the tipping material circumscribes the entire length of the "two-up" filter segment 300A, and a portion of the length of each tobacco rod 150A, 150B in the respective regions thereof adjacent the filter segment. Typically, that layer of tipping material 450 circumscribes about 3 mm to about 4 mm of the length of each tobacco rod. As such, a so called "two-up" cigarette 500 is provided. For certain preferred aspects, the tipping material may be selected from types of tipping material, and applied in a particular manner, comparable to that traditionally used for commercial filtered cigarette manufacture. Optionally, the cigarette can be air diluted (e.g., using laser perforation techniques) by forming at least one circumscribing ring of perforations through the layer of tipping material 450 and underlying plug wrap. Then, the "two-up" combined segment 300A is cut in half (i.e., through the "two-up" filter segment 300A along hashed line 2-2), perpendicular to its longitudinal axis, to provide two finished cigarettes 100A, 100B. As such, the two finished cigarettes 100A, 100B are each characterized by a smooth mouth end terminus, wherein the mouth end terminus of the filter material, plug wrap, and tipping material are all in the same plane.

Cigarette rods typically are manufactured using a cigarette making machine, such as a conventional automated cigarette rod making machine. Exemplary cigarette rod making machines are of the type commercially available from Molins PLC or Hauni-Werke Korber & Co. KG. For example, cigarette rod making machines of the type known as MkX (commercially available from Molins PLC) or PROTOS (commercially available from Hauni-Werke Korber & Co. KG) can be employed. A description of a PROTOS cigarette making machine is provided in U.S. Pat. No. 4,474,190 to Brand, at col. 5, line 48 through col. 8, line 3, which is incorporated herein by reference. Types of equipment suitable for the manufacture of cigarettes also are set forth in U.S. Pat. No. 4,781,203 to La Hue; U.S. Pat. No. 4,844,100 to Holznagel; U.S. Pat. No. 5,131,416 to Gentry; U.S. Pat. No. 5,156,169 to Holmes et al.; U.S. Pat. No. 5,191,906 to Myracle, Jr. et al.; U.S. Pat. No. 6,647,870 to Blau et al.; U.S. Pat. No. 6,848,449 to Kitao et al.; U.S. Pat. No. 6,904,917 to Kitao et al.; U.S. Pat. No. 7,210,486 to Hartmann; U.S. Pat. No. 7,275,548 to Hancock et al.; U.S. Pat. No. 7,281,540 to Barnes et al.; and U.S. Pat. No. 7,234,271 to Fitzgerald et al.; each of which is incorporated herein by reference.

The components and operation of conventional automated cigarette making machines will be readily apparent to those skilled in the art of cigarette making machinery design and operation. For example, descriptions of the components and operation of several types of chimneys, tobacco filler supply equipment, suction transport systems and garniture systems are set forth in U.S. Pat. No. 3,288,147 to Molins et al.; U.S.

Pat. No. 3,915,176 to Heitmann et al.; U.S. Pat. No. 4,291,713 to Frank; U.S. Pat. No. 4,574,816 to Rudszinat; U.S. Pat. No. 4,736,754 to Heitmann et al. U.S. Pat. No. 4,878,506 to Pinck et al.; U.S. Pat. No. 5,060,665 to Heitmann; U.S. Pat. No. 5,012,823 to Keritsis et al. and U.S. Pat. No. 6,360,751 to Fagg et al.; and U.S. Patent Publication No. 2003/0136419 to Muller; each of which is incorporated herein by reference. The automated cigarette making machines of the type set forth herein provide a formed continuous cigarette rod or smokable rod that can be subdivided into formed smokable rods of desired lengths.

Various types of cigarette components, including tobacco types, tobacco blends, top dressing and casing materials, blend packing densities and types of paper wrapping materials for tobacco rods, can be employed. See, for example, the various representative types of cigarette components, as well as the various cigarette designs, formats, configurations and characteristics, that are set forth in Johnson, Development of Cigarette Components to Meet Industry Needs, 52$^{nd}$ T.S.R.C. (September, 1998); U.S. Pat. No. 5,101,839 to Jakob et al.; U.S. Pat. No. 5,159,944 to Arzonico et al.; U.S. Pat. No. 5,220,930 to Gentry; U.S. Pat. No. 6,779,530 to Kraker; U.S. Pat. No. 7,237,559 to Ashcraft et al.; and U.S. Pat. No. 7,565,818 to Thomas et al.; and U.S. Patent Publication Nos. 2005/0066986 to Nestor et al. and 2007/0246055 to Oglesby; each of which is incorporated herein by reference. Most preferably, the entire smokable rod is composed of smokable material (e.g., tobacco cut filler) and a layer of circumscribing outer wrapping material.

Components for filter elements for filtered cigarettes typically are provided from filter rods that are produced using traditional types of rod-forming units, such as those available as KDF-2 and KDF-3E from Hauni-Werke Korber & Co. KG. Typically, filter material, such as filter tow, is provided using a tow processing unit. An exemplary tow processing unit has been commercially available as E-60 supplied by Arjay Equipment Corp., Winston-Salem, N.C. Other exemplary tow processing units have been commercially available as AF-2, AF-3, and AF-4 from Hauni-Werke Korber & Co. KG. In addition, representative manners and methods for operating a filter material supply units and filter-making units are set forth in U.S. Pat. No. 4,281,671 to Byrne; U.S. Pat. No. 4,862,905 to Green, Jr. et al.; U.S. Pat. No. 5,060,664 to Siems et al.; U.S. Pat. No. 5,387,285 to Rivers; and U.S. Pat. No. 7,074,170 to Lanier, Jr. et al. Other types of technologies for supplying filter materials to a filter rod-forming unit are set forth in U.S. Pat. No. 4,807,809 to Pryor et al. and U.S. Pat. No. 5,025,814 to Raker; which are incorporated herein by reference.

The filter material can vary, and can be any material of the type that can be employed for providing a tobacco smoke filter for cigarettes. Preferably a traditional cigarette filter material is used, such as cellulose acetate tow, gathered cellulose acetate web, polypropylene tow, gathered cellulose acetate web, gathered paper, strands of reconstituted tobacco, or the like. Especially preferred is filamentary tow such as cellulose acetate, polyolefins such as polypropylene, or the like. One filter material that can provide a suitable filter rod is cellulose acetate tow having 3 denier per filament and 40,000 total denier. As another example, cellulose acetate tow having 3 denier per filament and 35,000 total denier can provide a suitable filter rod. As another example, cellulose acetate tow having 8 denier per filament and 40,000 total denier can provide a suitable filter rod. For further examples, see the types of filter materials set forth in U.S. Pat. No. 3,424,172 to Neurath; U.S. Pat. No. 4,811,745 to Cohen et al.; U.S. Pat. No. 4,925,602 to Hill et al.; U.S. Pat. No. 5,225,277 to Takegawa et al. and U.S. Pat. No. 5,271,419 to Arzonico et al.; each of which is incorporated herein by reference.

Normally a plasticizer such as triacetin is applied to the filamentary tow in traditional amounts using known techniques. Other suitable materials or additives used in connection with the construction of the filter element will be readily apparent to those skilled in the art of cigarette filter design and manufacture. See, for example, U.S. Pat. No. 5,387,285 to Rivers.

The plug wrap can vary. See, for example, U.S. Pat. No. 4,174,719 to Martin. Typically, the plug wrap is a porous or non-porous paper material. Suitable plug wrap materials are commercially available. Exemplary plug wrap papers ranging in porosity from about 1,100 CORESTA units to about 26,000 CORESTA units are available from Schweitzer-Mauduit International as Porowrap 17-M1, 33-M1, 45-M1, 70-M9, 95-M9, 150-M4, 150-M9, 240M9S, 260-M4 and 260-M4T; and from Miquel-y-Costas as 22HP90 and 22HP150. Non-porous plug wrap materials typically exhibit porosities of less than about 40 CORESTA units, and often less than about 20 CORESTA units. Exemplary non-porous plug wrap papers are available from Olsany Facility (OP Paprina) of the Czech Republic as PW646; Wattenspapier of Austria as FY/33060; Miquel-y-Costas of Spain as 646; and Schweitzer-Mauduit International as MR650 and 180. Plug wrap paper can be coated, particularly on the surface that faces the filter material, with a layer of a film-forming material. Such a coating can be provided using a suitable polymeric film-forming agent (e.g., ethylcellulose, ethylcellulose mixed with calcium carbonate, nitrocellulose, nitrocellulose mixed with calcium carbonate, or a so-called lip release coating composition of the type commonly employed for cigarette manufacture). Alternatively, a plastic film (e.g., a polypropylene film) can be used as a plug wrap material. For example, non-porous polypropylene materials that are available as ZNA-20 and ZNA-25 from Treofan Germany GmbH & Co. KG can be employed as plug wrap materials.

Cigarette filter rods can be used to provide multi-segment filter rods. Such multi-segment filter rods then can be employed for the production of filtered cigarettes possessing multi-segment filter elements. An example of a two-segment filter element is a filter element possessing a first cylindrical segment incorporating activated charcoal particles dispersed within cellulose acetate tow (e.g., a "dalmation" type of filter segment) at one end, and a second cylindrical segment that is produced from a filter rod produced essentially of flavored, plasticized cellulose acetate tow filter material at the other end. The production of multi-segment filter rods can be carried out using the types of rod-forming units that traditionally have been employed to provide multi-segment cigarette filter components. Multi-segment cigarette filter rods can be manufactured using a cigarette filter rod making device available under the brand name Mulfi from Hauni-Werke Korber & Co. KG of Hamburg, Germany. Representative types of filter designs and components, including representative types of segmented cigarette filters, are set forth in U.S. Pat. No. 4,920,990 to Lawrence et al.; U.S. Pat. No. 5,012,829 to Thesing et al.; U.S. Pat. No. 5,025,814 to Raker; U.S. Pat. No. 5,074,320 to Jones et al.; U.S. Pat. No. 5,105,838 to White et al.; U.S. Pat. No. 5,271,419 to Arzonico et al.; U.S. Pat. No. 5,360,023 to Blakley et al.; U.S. Pat. No. 5,396,909 to Gentry et al.; U.S. Pat. No. 5,718,250 to Banerjee et al.; U.S. Pat. No. 6,761,174 to Jupe et al.; and U.S. Pat. No. 7,240,678 to Crooks et al.; U.S. Patent Application Publication Nos. 2004/0261807 to Dube et al. and 2007/0056600 to Coleman III, et al.; PCT Publication No. WO 03/009711 to Kim; and PCT Publication No. WO 03/047836 to Xue et al.; which are incorporated herein by reference.

The length of the filter element of each cigarette can vary. Typically, the overall length of a filter element is about 20 mm to about 40 mm, and often about 25 mm to about 35 mm. For a typical dual-segment filter element, the downstream or mouth end filter segment often has a length of about 10 mm to about 20 mm; and the upstream or tobacco rod end filter segment often has a length of about 10 mm to about 20 mm.

Filter elements, or filter segment components of combination filters, typically are provided from filter rods that are manufactured using traditional types of cigarette filter rod making techniques. For example, so-called "six-up" filter rods, "four-up" filter rods and "two-up" filter rods that are of the general format and configuration conventionally used for the manufacture of filtered cigarettes can be handled using conventional-type or suitably modified cigarette rod handling devices, such as tipping devices available as Lab MAX, MAX, MAX 2, MAX S, MAX 80 or MAX 90 from Hauni-Werke Korber & Co. KG. See, for example, the types of devices set forth in U.S. Pat. No. 3,308,600 to Erdmann et al.; U.S. Pat. No. 4,281,670 to Heitmann et al.; U.S. Pat. No. 4,280,187 to Reuland et al.; U.S. Pat. No. 4,850,301 to Greene, Jr. et al.; U.S. Pat. No. 6,229,115 to Vos et al.; U.S. Pat. No. 7,434,585 to Holmes; and U.S. Pat. No. 7,296,578 to Read, Jr.; and U.S. Patent Application Publication No. 2006/0169295 to Draghetti, each of which is incorporated herein by reference. The operation of those types of devices will be readily apparent to those skilled in the art of automated cigarette manufacture. Manners and methods for applying adhesives to tipping materials during automated cigarette manufacture will be apparent to those skilled in the art of cigarette design and manufacture. For example, a filtered cigarette can be tipped with a first layer of tipping material in an essentially traditional manner using a Lab MAX tipping device that is available from Hauni-Werke Korber & Co. KG, and that tipped cigarette can be collected and tipped again using that device (e.g., using the device in an essentially traditional manner, or in a suitably modified manner to provide a desired pattern of adhesive application) in order to provide a filtered cigarette possessing two or more layers of tipping material, if necessary or desired.

In instances of a single layer of tipping material, the tipping material most preferably extends over the entire length of the filter element, and about 2 mm to about 6 mm, often about 3 mm to about 5 mm, and frequently about 4 mm over the length of the adjacent region of the tobacco rod. The tipping material that is used for any of the one or more tipping material layers can vary. In certain preferred aspects, the material used as the tipping material has the characteristics and qualities commonly associated with cigarette tipping materials known in the art. Typical tipping materials are papers exhibiting relatively high opacities. Representative tipping materials have TAPPI opacities of greater than about 81 percent, often in the range of about 84 percent to about 90 percent, and sometimes greater than about 90 percent. Typical tipping materials are printed with inks, typically nitrocellulose based, which can provide for a wide variety of appearances and "lip release" properties. Representative tipping papers or materials have basis weights ranging from about 25 m/m$^2$ to about 60 g/m$^2$, often about 30 g/m$^2$ to about 40 g/m$^2$. Representative tipping papers are available as Tervakoski Reference Nos. 3121, 3124, TK652, TK674, TK675, A360 and A362; and Schweitzer-Mauduit International Reference Nos. GSR270 and GSR265M2. See also, for example, the types of tipping materials, the methods for combining cigarette components using tipping materials, and techniques for wrapping various portions of cigarettes using tipping materials, that are set forth in U.S. Patent Application Publication No. 2007/0215167 to Crooks et al.

Adhesives used to secure tipping materials to each other or to other filtered cigarette components can vary. Typical exemplary adhesive formulations that are used for application of tipping material to other cigarette components in commercial filtered cigarette manufacturing operations are water-based emulsions incorporating mixtures of ethylene vinyl acetate copolymers and polyvinylacetate. Representative adhesives that are useful for applying tipping materials to cigarette components are available as Reference Nos. 32-2049 and 32-2124 from National Starch & Adhesives Corp. See also, for example, Skeist, Handbook of Adhesives, 2$^{nd}$ Edition (1977); Schneberger, Adhesive in Manufacturing (1983); Gutcho, Adhesives Technology Developments Since 1979 (1983); Landrock, Adhesives Technology Handbook (1985); and Flick, Handbook of Adhesives Raw Materials, 2$^{nd}$ Edition (1989).

Cigarettes can be air diluted. Tipping materials can be pre-perforated, or air diluted on-line using laser perforation techniques. For cigarettes that are air diluted or ventilated, the amount or degree of air dilution or ventilation can vary. Frequently, the amount of air dilution for an air diluted cigarette is greater than about 10 percent, generally is greater than about 20 percent, often is greater than about 30 percent, and sometimes is greater than about 40 percent. Typically, the upper level for air dilution for an air diluted cigarette is less than about 80 percent, and often is less than about 70 percent. As used herein, the term "air dilution" is the ratio (expressed as a percentage) of the volume of air drawn through the air dilution provisions to the total volume and air and smoke drawn through the cigarette and exiting the extreme mouth end portion of the cigarette.

Figure 3:
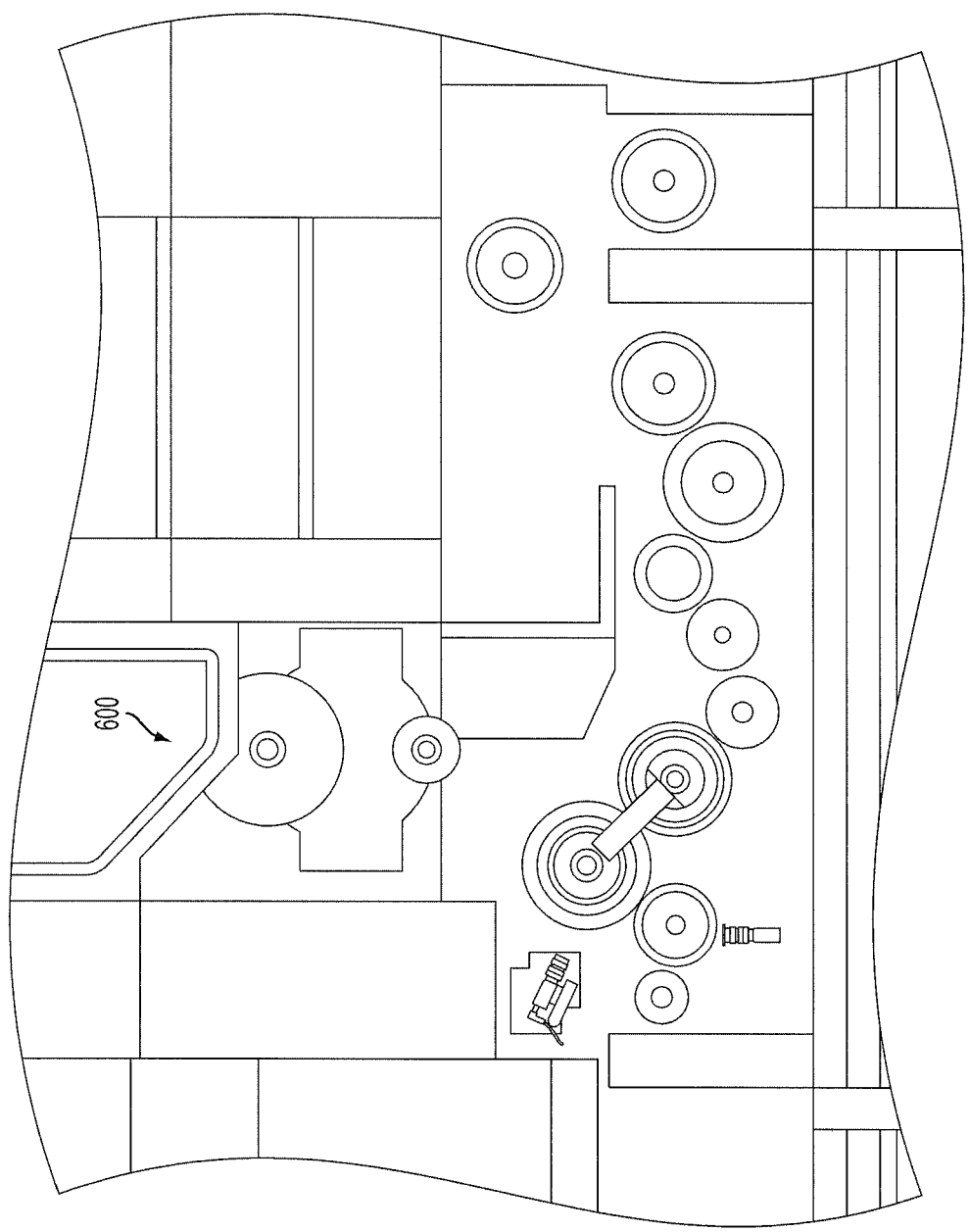
FIGS. 3 through 5 are progressively magnified side elevations of a filtered smoking article inspection system for a smoking article, according to one aspect of the disclosure.
Figure 4:
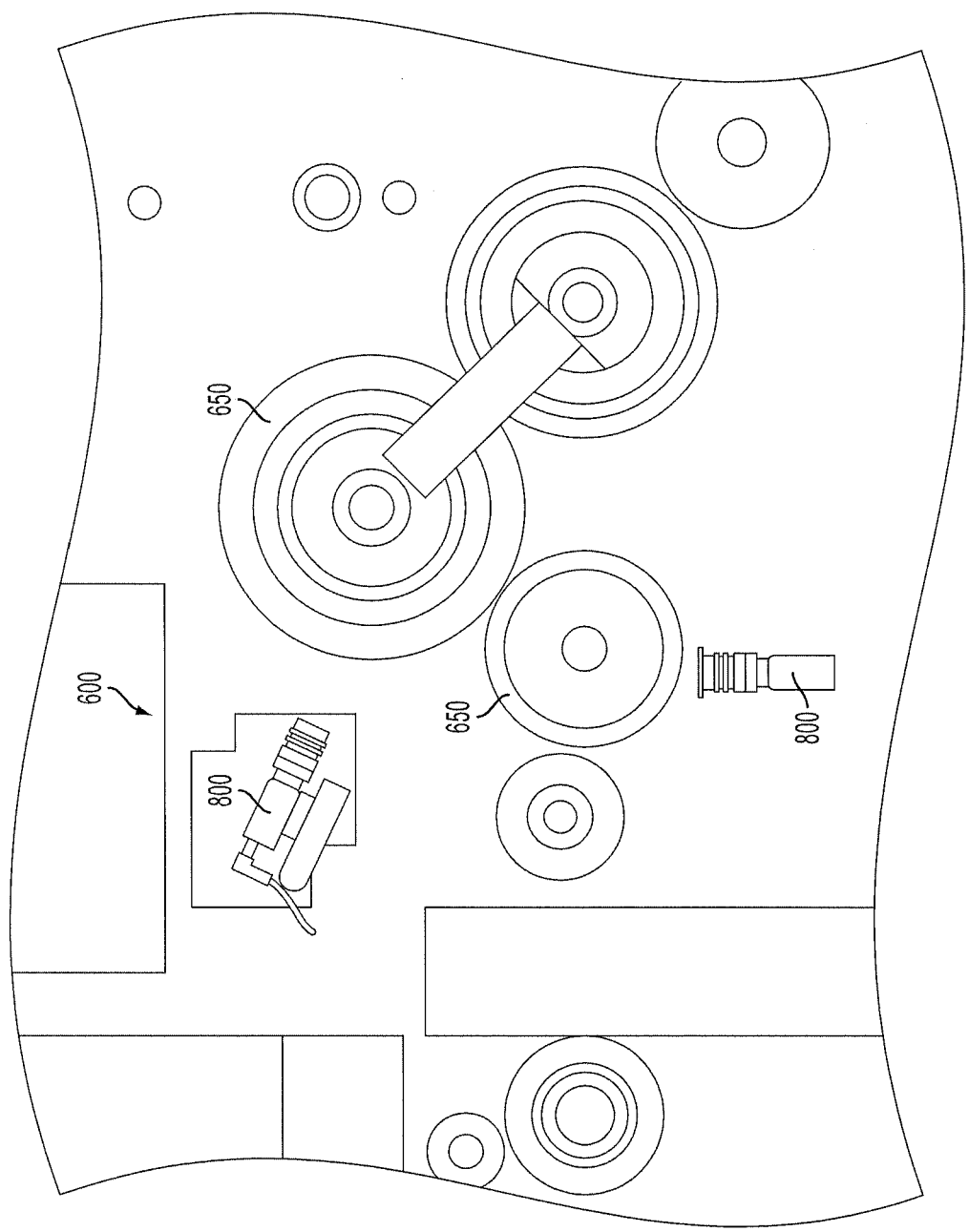
Figure 5:
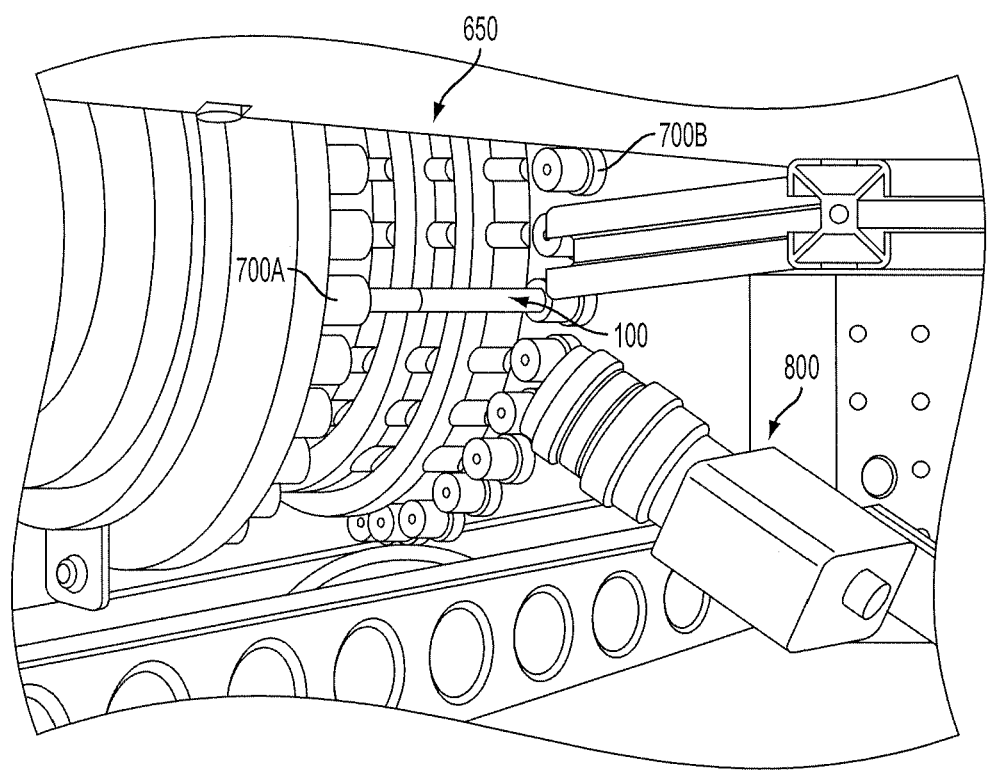

Referring to FIGS. 3-5, some conventional-type or suitably modified tipping devices 600 such as, for example, a Lab MAX, MAX, MAX 2, MAX S, MAX 80 or MAX 90 tipping device from Hauni-Werke Korber & Co. KG, are configured with one or more substantially cylindrical rotatable devices 650 (i.e., a drum, cylinder, etc.) defining longitudinal channels or otherwise including longitudinally-arranged securing mechanisms for receiving individual filter element/tobacco rod assemblies (smoking articles 100) and for transporting the assemblies 100 in a machine direction, which may be, for example, in the direction of rotation of the rotatable device about the longitudinal axis thereof. For example, in some instances, each rotatable device 650 may have a plurality of securing mechanisms operably engaged therewith and angularly spaced apart about the cylindrical surface thereof. Each securing mechanism may comprise, for example, contact members 700A, 700B spaced apart along the axis of the rotatable device 650 by about the length of the filter element/tobacco rod assembly 100.

As previously disclosed, a smoking article includes a filter element having a mouth end terminus, and a smokable rod having a lighting end terminus opposite from the filter element, wherein the smokable rod includes a smokable material having a circumscribing outer layer of a wrapping material, and wherein the smokable rod and filter element are serially secured to each other by a tipping material circumscribing the filter element along a longitudinal periphery thereof and the smokable rod along a portion of a longitudinal periphery thereof adjacent to the filter element to form the assembly or smoking article 100. With such tipping devices 600, an assembly 100 may be received between the contact members 700A, 700B, and secured with respect to the rotatable device 650, for example, through a friction fit between the contact members 700A, 700B or through a vacuum applied to the filter element/tobacco rod assembly 100 through either or both of the contact members 700A, 700B. In one aspect, the rotatable device 650 may be configured such that the tipping material associated with each smoking article received thereby is accessible at least about the portion of the longitudinal periphery of the smoking article to which it is applied.

In some instances, one rotatable device 650 associated with the tipping device 600 may be configured to be actively engaged in the application of the tipping material (paper) about the filter element/tobacco rod interface. In such instances, for example, that rotatable device 650 may be configured to receive the assembly 100 after an adhesive has been applied to the tipping paper seam line, or the adhesive may be applied to the tipping paper seam line after being received by the rotatable device 650. In other instances, the rotatable device 650 may receive the assembly 100, from a previous, serially-disposed, rotatable device 650, for inspection and/or for removing rejected assemblies 100 from the production process, wherein the transfer of the assembly 100 therebetween also forwards the assembly 100 along the tipping device in a machine direction. As such, the tipping device may also comprise a transport device configured to transport individual as-formed smoking articles (assemblies 100) from a first position to a second position in a machine direction.

Upon the tipping device 600 executing the filtered smoking article tipping process, the manufacture of the smoking article 100 is essentially complete. As such, an opportunity may be present to examine each of the assemblies 100 for any apparent defects. Some such apparent defects may include, for example, tipping material that is misaligned with respect to the smoking article (i.e., forming a spiral instead of a cylinder when wrapped about the smoking article), wrapping material that is misaligned with respect to the smokable material, tipping material or wrapping material that is wrinkled, tipping material or wrapping material that is visibly contaminated (i.e., spots or other undesirable discolorations or stains), the wrong tipping material (i.e., the actual tipping material may not correspond to the specified material), the wrong wrapping material, multiple units of the tipping material applied to the smoking article (i.e., units of the tipping paper, in excess of the specified amount, may get stuck together and applied about the smoking article), multiple units of the wrapping material applied to the smokable material, adhesive securing the tipping material that is unevenly applied about the smoking article or tipping material that is inconsistently adhered to the smoking article (or overlapping ends of the tipping paper that are not securely adhered together), overlapping ends of the wrapping material that are not securely adhered together (thus exposing the smokable material), tipping material that is rolled over itself along the portion of the longitudinal periphery of the smokable rod (i.e., forming a raised "collar" about the smoking article), tipping material that does not completely secure the tobacco rod to the filter element (i.e., the tobacco rod may not be secured to and may thus easily separate from the filter element), tipping material that does not extend at least along the portion of the longitudinal periphery of the smokable rod, as specified, wrapping material that has been punctured (i.e., torn, pulled, or had a hole formed therein, for instance, by stem portions in the tobacco material comprising the smokable material) to expose the smokable material, and (excess) adhesive securing one of the tipping material about the smoking article and the wrapping material about the smokable material that is exposed.

In this regard, there may exist some methods for evaluating the completed smoking article for defects. For example, in one instance, a pressure/vacuum or airflow test could be conducted on the smoking article, via the contact members 700A, 700B, while the smoking article 100 is secured to the rotatable device 650 thereby. More particularly, an air flow or a vacuum/pressure may be directed through either or both of the contact members 700A, 700B to interact with the smoking article secured therebetween. The measured effect of the interaction may be used to infer certain defects in the smoking article, but may not be useful to determine certain other defects. For example, an airflow/pressure/vacuum test may be useful in determining whether the tipping paper is properly adhered about the filter element/tobacco rod interface (i.e., if a specified vacuum cannot be maintained across the smoking article, there may be a leak about the filter element/tobacco rod interface due to improperly adhered tipping paper). However, the same airflow/pressure/vacuum test may not be able to determine whether the tipping material is misaligned, wrinkled, rolled over, or contaminated. In some instances, the airflow/pressure/vacuum test may not even be conducted, for example, where improperly adhered tipping paper about the filter element/tobacco rod interface may be evidenced by the inability to secure the smoking article between the contact members 700A, 700B. In such cases, the defective smoking article may just remove itself from the rotatable device 650, and thus the smoking article manufacturing process, on its own. A further issue is that such methods of determining whether defects exist in manufactured smoking articles may not necessarily have the capability of determining the particular type of defect in each smoking article found to be defective. As such, by not necessarily being able to identify the particular type of defect, the method may not be able to indicate when corrective action must be taken in an upstream process during manufacture of the smoking article, or even the particular upstream process requiring such corrective action, to eliminate the apparent defects.

As such, in one aspect of the present disclosure, an inspection device, such as an imaging device 800 may be operably engaged with the transport device (tipping device 600) and configured to optically inspect each smoking article 100 at least about the portion of the longitudinal periphery of the smoking article having the tipping material as the smoking article is transported between the first and second positions in the machine direction. More particularly, one or more imaging devices 800 may be disposed adjacent to one or more of the rotatable devices 650, with each imaging device 800 being configured to capture one or more images of each smoking article 100 secured by the rotatable device 650 disposed adjacent thereto, as the smoking articles are transported therepast from the first position to the second position (i.e., to the subsequent rotatable device or other downstream device) in the machine direction. In such instances, the imaging device 800 may be disposed adjacent to the rotatable device 650 and be configured to be capable of capturing one or more images of a portion (i.e., half) of the circumference of each smoking article. That is, when a smoking article is secured by the rotatable device 650, about half of the circumference of the smoking article will be visible externally to the rotatable device 650. Upon transfer of the smoking article to a subsequent rotatable device 650, the portion of the circumference of the smoking article not previously visible externally to the previous rotatable device 650 will now be visible with respect to the subsequent rotatable device 650. As such, another imaging device 800 may be disposed adjacent to the subsequent rotatable device 650, and configured to capture one or more images of the previously not-visible portion of the smoking article 100. Combining the images from the two imaging devices 800 may thus provide complete imaging of the entire circumference of the smoking article, or at least about the circumference of the smoking article to the axial extent of the tipping paper (i.e., about the filter element/ tobacco rod interface). In some instances, as shown in FIG. 6, a display terminal 850 may be operably engaged with the imaging device 800 of the inspection device, wherein the display terminal 850 may be configured to display the at least one image of each smoking article 100.

In other aspects of the disclosure, the smoking article 100 may be supported in different manners so as to allow the inspection device to perform the optical inspection thereof. For example, the smoking article may be supported by, or independently of, the rotatable device 650. In some such instances, the smoking article may be supported by engagement with the filter element only (i.e., via the mouth end terminus) or by the tobacco rod only (i.e., via the lighting end terminus). In still other aspects, the smoking article may be supported such that the imaging device 800 moves about the smoking article to perform the optical inspection thereof. In yet other aspects, the contact members 700A, 700B of a rotatable device 650 may be configured to rotate in concert with respect to the rotatable device 650 so as to rotate the smoking article about the longitudinal axis thereof while the smoking article is secured to the rotatable device 650.

Figure 6:
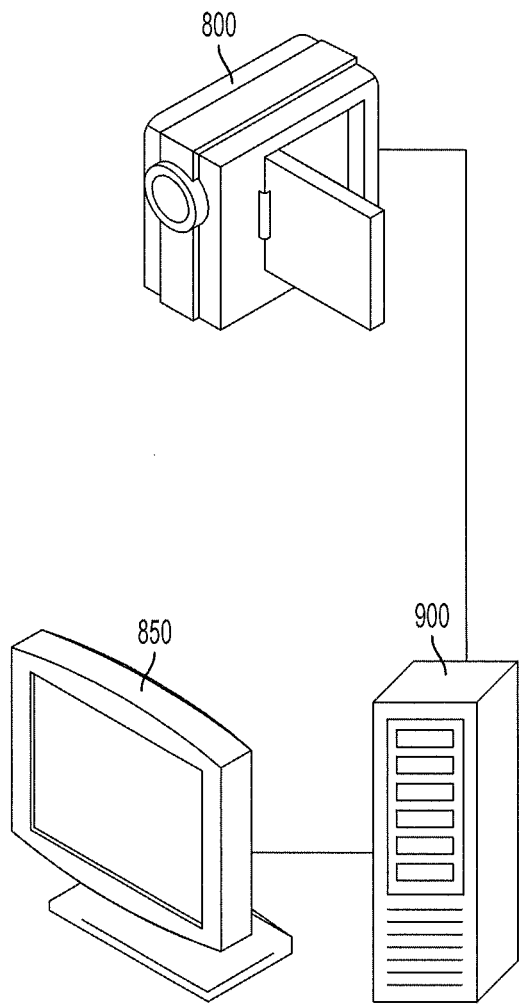
FIG. 6 is a schematic view of components of an inspection device associated with a filtered smoking article inspection system for a smoking article, according to one aspect of the disclosure.

In one aspect, in addition to the display terminal 850 as shown in FIG. 6, the inspection device may further comprise a computer device 900 configured to automatically process the at least one image from the imaging device(s) 800 to determine whether the inspected smoking article is defective. More particularly, in some instances, the inspection device may comprise or include a high speed monochrome (or color) camera (Model No. CV-H035M), a monitor (Model No. CA-MP81), a PLC Model No. (KV-16AT), and a high speed vision system (Model No. CV-5502), all from Keyence Corporation. In one configuration, the inspection system may be implemented to perform a "machine vision" analysis of the smoking articles with an inspection speed (i.e., processing time per smoking article inspection) of less than about 10 milliseconds, and preferably less than about 5 milliseconds. That is, the computer device 900, such as the vision system, may be configured to analyze the one or more images of the area of the smoking article wrapped by the tipping paper, whether individually or collectively, to determine whether any defects exist in the completed product.

For example, the computer device 900 may be programmed with examples of various defects which may be discovered during the manufacture of the smoking article. In those instances, the one or more images captured by the imaging device 800 can then be compared to the exemplary defects by the computer device 900. As such, if the computer device 900 matches the one or more images of a particular smoking article to one of the exemplary defects, to a reasonable certainty, then the particular smoking article may be determined to be defective. In another example, the computer device 900 may be programmed with one or more examples of non-defective smoking articles. In those instances, the one or more images of the smoking article being inspected may then be compared to the non-defective examples by the computer device 900. As such, if the computer device 900 does not matches the one or more images of a particular smoking article to one of the non-defective examples, to a reasonable certainty, then the particular smoking article may be determined to be defective. One skilled in the art, however, will appreciate that a "machine vision" inspection or other automated evaluation of the one or more images of the smoking article may be accomplished in many different manners and, as such, the examples presented herein are not intended to be limiting. For example, the one or more images may be "stitched" together or otherwise combined to form a continuous reconstructed image of the tipping paper circumscribing the smoking article, wherein the reconstructed image can then be compared to an exemplary tipping paper specimen determined to be defect-free.

As a result of the disclosed optical inspection/machine vision evaluation of the substantially completed smoking article in the tipping device 600, aspects of the disclosed filtered smoking article inspection system may be capable of particularly determining and/or identifying, from the optical inspection thereof, certain apparent defects in the smoking articles such as, for example, tipping material that is misaligned with respect to the smoking article; wrinkled tipping material; tipping material that may be dirty, stained, or otherwise visibly contaminated; tipping material comprising a non-specified or otherwise incorrect material; multiple units of the tipping material applied to the smoking article; tipping material rolled over itself along the portion of the longitudinal periphery of the smokable rod; and/or tipping material that does not extend at least along the portion of the longitudinal periphery of the smokable rod as specified. In some instances, aspects of the filtered smoking article inspection system may also be capable of particularly determining, for instance, whether the tipping material is completely adhered about the smoking article, and/or whether a tobacco rod is properly secured to the filter element by the tipping material, either using the disclosed optical inspection/machine vision evaluation alone, or in conjunction with another inspection process such as the aforementioned airflow/pressure/vacuum test. For the latter, it may be determined, for example, that if no defects in the smoking article are apparent from the optical inspection thereof, but the smoking article fails the airflow/pressure/ vacuum test, then there exists a defect likely related to the adherence of the tipping material about the filter element/ tobacco rod interface or along the tipping material seam line.

In some aspects, a defective smoking article, identified as such by the filtered smoking article inspection system, may be removed from the process prior to that defective smoking article being packaged for further distribution. As previously disclosed, such a defective smoking article may not necessarily be securable to the rotatable device 650 via the contact members 700A, 700B. In other instances, the defective smoking article may be released from the rotatable device 650 at an appropriate point as the rotatable device advances that defective smoking article from the first position to (or past) the second position. For example, the defective smoking article may be deposited in a reject receptacle, or directed to a re-work process, depending on the particular defect identified. In other instances, the defective smoking article may be removed from the rotatable device 650 by a selection device (i.e., a subsequent rotatable device 650 or other mechanism for receiving the defective smoking article from the previous rotatable device 650) operably engaged therewith. In some aspects, the directing the defective smoking article in a desired manner to a subsequent process for handling such defective smoking articles may be accomplished in response to the computer device 900 associated with the inspection device. In addition, aspects of the filtered smoking article inspection system may be configured to monitor the determined defects found in the smoking articles, for example, by amount and/or frequency, and communicating the results or otherwise directing appropriate corrective action be taken, if a selected threshold is attained (i.e., whether to address an upstream process, to address a material issue, or to address a source of contamination).

Figure 7:
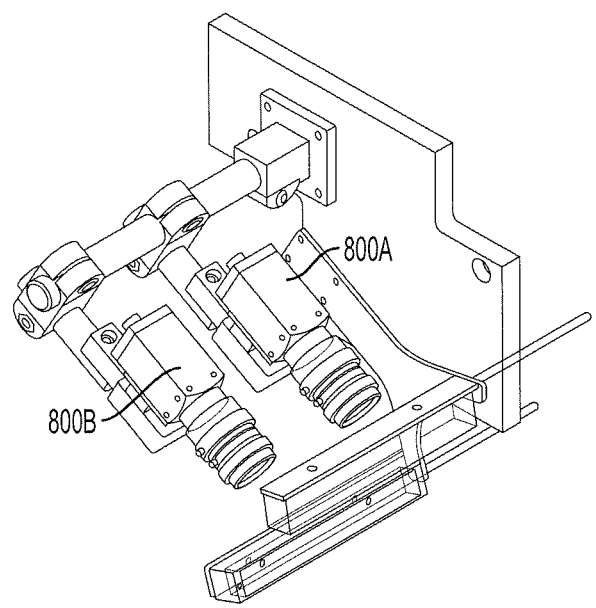
FIG. 7 is a schematic view of an inspection device associated with a filtered smoking article inspection system for a smoking article, according to another aspect of the disclosure, wherein one or more imaging devices are implemented and cooperate to capture one or more images of substantially the entire length of a smoking article.

Many modifications and other aspects of the disclosure will come to mind to one skilled in the art to which this disclosure pertains having the benefit of the teachings presented in the foregoing description; and it will be apparent to those skilled in the art that variations and modifications of the present disclosure can be made without departing from the scope or spirit of the disclosure. For example, as shown in FIG. 7, the concept of applying an optical inspection/machine vision evaluation of the filter element/tobacco rod interface as it relates to the application of the tipping material may also be extended to include an optical inspection/machine vision evaluation of the remainder of the tobacco rod, as well. That is, in instances where one imaging device 800A is implemented adjacent to a rotation device to capture one or more images of the filter element/tobacco rod interface as it relates to the application of the tipping material, a second imaging device 800B may be disposed adjacent to the first imaging device so as to be capable of capturing one or more images of the remaining tobacco rod portion of the smoking article at the same inspection point. Both imaging devices 800A, 800B are configured to interface with the computer device 900 to implement the machine vision functionality, and may also be in communication with the display terminal 850. More particularly, as will be appreciated by one skilled in the art, the computer device 900 may also be configured to compare the one or more images of the tobacco rod portion captured by the second imaging device 800B to examples of defective (or non-defective) tobacco rods, in order to determine whether a defect exists in the tobacco rod (wherein exemplary defects have been previously noted herein). Further, in some aspects, the one or more images captured by the first and second imaging devices 800A, 800B may be concurrently analyzed by the computer device 900 to evaluate other parameters of the smoking article such as, for example, the overall length. Therefore, it is to be understood that the disclosure is not to be limited to the specific aspects disclosed and that modifications and other aspects are intended to be included within the scope of the appended claims. Although specific terms are employed herein, they are used in a generic and descriptive sense only and not for purposes of limitation.

What is claimed is:

1. A filter smoking article inspection system for a smoking article comprising a filter element having a mouth end terminus and a smokable rod having a lighting end terminus opposite from the filter element, the smokable rod including a smokable material having a circumscribing outer layer of a wrapping material, the smokable rod and filter element being serially secured to each other by a tipping material circumscribing the filter element along a longitudinal periphery thereof and the smokable rod along a portion of a longitudinal periphery thereof adjacent to the filter element, said inspection system comprising:

a transport device configured to transport individual as-formed smoking articles from a first position to a second position such that the tipping material associated with each smoking article is accessible at least about the portion of the longitudinal periphery of the smoking article; and an inspection device operably engaged with the transport device and configured to optically inspect each smoking article at least about the portion of the longitudinal periphery of the smoking article having the tipping material as the smoking article is transported between the first and second positions, the inspection device being configured to automatically determine from the optical inspection whether the inspected smoking article is defective, wherein the inspection device is further configured to determine whether a defect exists in the smoking articles from the optical inspection thereof, the defect being determined according to whether the tipping material is misaligned with respect to the smoking article, whether the wrapping material is misaligned with respect to the smokable material, whether one or the tipping material and the wrapping material is wrinkled, whether one of the tipping material and the wrapping material is visibly contaminated, whether one of the tipping material and the wrapping material corresponds to a specified material, whether multiple units of the tipping material have been applied to the smoking article, whether multiple units of the wrapping material have been applied to the smokable material, whether the tipping material is adhered as specified about the smoking article, whether the wrapping material is adhered as specified about the smokable material, whether the tipping material is rolled over itself along the portion of the longitudinal periphery of the smoking article, whether the tobacco rod is secured to the filter element by the tipping material, whether the tipping, material extends at least along the portion of the longitudinal periphery of the smokable rod as specified, whether the wrapping material has been punctured to expose the smokable material, and whether adhesive securing one of the tipping material about the smoking article and the wrapping material about the smokable material is exposed.

2. The system according to claim 1, wherein the mouth end terminus of the filter element and the lighting end terminus of the smokable rod extend substantially perpendicularly to a longitudinal axis of the smoking article, and the transport device is configured to engage at least one of the mouth end terminus of the filter element and the lighting end terminus of the smokable rod of the smoking article to support the smoking article during movement from the first position to the second position without contacting the longitudinal periphery if the smoking article.

3. A system according to claim 1 , further comprising a rotation device operably engaged with the transport device, the rotation device being configured to rotate the smoking article about a longitudinal axis thereof so as to allow the inspection device to inspect the smoking article at least about the portion of the longitudinal periphery of the smoking article having the tipping material.

4. A system according to claim 1, wherein the inspection device comprises an imaging device configured to capture at least one image of each smoking article, at least about the portion of the longitudinal periphery orate smoking article having the tipping material, as the smoking article is transported between the first and second positions.

5. A system according to claim 4, further comprising a display terminal operably engaged with the imaging device and configured to display the at least one image of each smoking article.

6. A system according to claim 4, wherein the inspection device further composes a computer device configured to automatically process the at least one image from the imaging device to determine whether the inspected smoking article is defective.

7. A system according to claim 1, further comprising a selection device operably engaged with the transport device, the selection device being responsive to the inspection device to remove any smoking article determined to be detective by the inspection device.

8. A system according to claim 1, wherein the inspection device is configured to determine, from the optical inspection of each smoking article, whether the smoking article corresponds to a non-defective smoking article.

9. A system according to claim 1, wherein the transport device includes a rotatable cylinder further configured to retain an individual smoking article about an outer surface thereof as the smoking article is transported between the first and second positions.

10. A system according to claim 9, wherein the inspection device further comprises an imaging device disposed adjacent to the rotatable cylinder, and wherein the imaging device is configured to optically inspect each smoking article at least about the portion of the longitudinal periphery of the smoking article having the tipping material as the smoking article is transported therepast upon rotation of the cylinder.

11. A system according to claim 1, wherein the smoking article is supported by engagement of the transport device with only the mouth end terminus.

12. A system according to claim 1, wherein the smoking article is supported by engagement of the transport device with only the lighting end terminus.

13. A system according in claim 1, wherein the transport device comprises one or more contact member configured to engage at least one of the mouth end terminus of the filter element and the lighting end terminus of the smokable rod of the smoking, and respectively rotate about a rotational axis that is substantially coaxial with the longitudinal axis of the smoking article engaged therewith.

14. A method of inspecting a smoking article comprising a filter element having a mouth end terminus and a smokable rod having a lighting end terminus opposite from the filter element, the smokable rod including a smokable material having a circumscribing outer liver of a wrapping material, the smokable rod and filter element being serially secured to each other by a tipping material circumscribing the filter element along a longitudinal periphery thereof and the smokable rod along a portion of a longitudinal periphery thereof adjacent to the filter element said method comprising:
    transporting individual as-formed smoking articles from a first position to a second position with a transport device such that the tipping material associated with each smoking article is accessible at least about the portion of the longitudinal periphery of the smoking article;
    optically inspect g each smoking article with an inspection device, at least about the portion of the longitudinal periphery of the smoking article having the tipping material, is the smoking article is transported between the first and second positions, and automatically determining whether the inspected smoking article is defective, with the inspection device, from the optical inspection thereof; and
    determining whether a defect exists in the smoking articles from the optical inspection thereof, the defect be determined according to whether the tipping material is misaligned with respect to the smoking article, whether the wrapping material is misaligned with respect to the smokable material, whether one of the tipping material and the wrapping material is wrinkled. whether one of the tipping material and the wrapping material is visibly contaminated, whether one of the tipping material and the wrapping material corresponds to a specified material, whether multiple units of the tipping material have been applied to the smoking article, whether multiple units of the wrapping material have been applied to the smokable material whether the tipping material is adhered as specified about the smoking article, whether the wrapping material is adhered as specified about the smokable material, whether the tipping material is rolled over itself along the portion of the longitudinal periphery of the smoking article, whether the tobacco rod is secured to the filter clement by the tipping material, whether the tipping material extends at least along the portion of the longitudinal periphery of the smokable rod as specified, whether the wrapping material has been punctured to expose the smokable material, and whether adhesive securing one of the tipping material about the smoking article and the wrapping material about the smokable material is exposed.

15. A method according to claim 14. wherein the mouth end terminus of the filter element and the lighting end terminus of the smokable rod extend substantially perpendicularly to a longitudinal axis of the smoking article, and wherein
    transporting individual as-formed smoking articles from the first position to the second position with the transport device comprises engaging at least one of the mouth end terminus of the filter element and the lighting end terminus of the smokable rod of the smoking article with the transport device to support the smoking article during movement from the first position to the second position without contacting the longitudinal periphery of the smoking article.

16. A method according to claim 14, further comprising rotating the smoking article about a longitudinal axis thereof with a rotation device operably engaged with the transport device so as to allow the inspection device to inspect the smoking article at least about the portion of the longitudinal periphery of the smoking article having the tipping material.

17. A method according to claim 14, further comprising capturing at least one image of each smoking article with an imaging device, at least about the portion of the longitudinal periphery of the smoking article having the tipping material, as the smoking article is transported between the first and second positions.

18. A method according to claim 17, further comprising displaying the at least one image of each smoking article on a display terminal operably engaged with the imaging device.

19. A method according to claim 17, further comprising: automatically processing the at least one image from the imaging device with a computer device to determine whether the inspected smoking article is defective.

20. A method according to claim 14, further comprising removing any smoking article determined to be defective with a selection device operably engaged with the transport device, in response to the determination thereof by the inspection device.

21. A method according to claim 14 further comprising determining, from the optical inspection of each smoking article, whether the smoking article corresponds to a non-defective smoking article.

22. A method according to claim 14, wherein the transport device includes a rotatable cylinder, and the method further comprises retaining an individual smoking article about an outer surface of the rotatable cylinder as the smoking article is transported between the first and second positions.

23. A method according to claim 22, wherein the inspection device further comprises an imaging device disposed adjacent to the rotatable cylinder, and the method further comprises optically inspecting each smoking article with the imaging device, at least about the portion of the longitudinal periphery of the smoking article having the tipping material, as the smoking article is transported therepast upon rotation of the cylinder.

24. A method according to claim 15, wherein engaging, at least one of the mouth end terminus of the filter element and the lighting end terminus of the smokable rod of the smoking article comprises engaging only the mouth end terminus.

25. A method according to claim 15, wherein engaging at least one of the mouth end terminus of the filter element and the lighting end terminus of the smokable rod of the smoking article comprises engaging only the lighting end terminus.

26. A method according to claim 15, wherein engaging at least one of the mouth end terminus of the filter element and the lighting end terminus of the smokable rod of the smoking article comprises engaging at least one of the mouth end terminus of the filter element and the lighting end terminus of the smokable rod of the smoking article with one or more contact members and respectively rotating the contact members about a rotational axis that is substantially coaxial with the longitudinal axis of the smoking article engaged therewith.

\* \* \* \* \*

UNITED STATES PATENT AND TRADEMARK OFFICE
CERTIFICATE OF CORRECTION

Page 1 of 2

PATENT NO.        : 8,760,508 B2
APPLICATION NO.   : 12/686489
DATED             : June 24, 2014
INVENTOR(S)       : Franklin Forrest Brantley et al.

It is certified that error appears in the above-identified patent and that said Letters Patent is hereby corrected as shown below:

In the Claims

In Claim 1, column 17, line 42, please change "filter" to --filtered--.

In Claim 1, column 18, line 7, please change "or" to --of--.

In Claim 2, column 18, line 38, please change "if" to --of--.

In Claim 4, column 18, line 50, please change "orate" to --of the--.

In Claim 6, column 18, line 58, please change "composes" to --comprises--.

In Claim 7, column 18, line 65, please change "detective" to --defective--.

In Claim 13, column 19, line 23, please change "in" to --to--.

In Claim 13, column 19, line 24, please change "member" to --members--.

In Claim 14, column 19, line 34, please change "liver" to --layer--.

In Claim 14, column 19, line 45, please change "inspect g" to --inspecting--.

In Claim 14, column 19, line 48, please change ", is" to --as--.

In Claim 14, column 19, line 54, please change "be" to --being--.

In Claim 14, column 19, line 59, please change "wrinkled." to --wrinkled,--.

Signed and Sealed this
Thirtieth Day of September, 2014

Michelle K. Lee
*Deputy Director of the United States Patent and Trademark Office*

CERTIFICATE OF CORRECTION (continued)
U.S. Pat. No. 8,760,508 B2

In Claim 14, column 19, line 66, please change "material whether" to --material, whether--.

In Claim 14, column 20, line 5, please change "clement" to --element--.

In Claim 15, column 20, line 13, please change "14." to --14,--.

In Claim 19, column 20, line 41, please change "comprising:" to --comprising--.

In Claim 24, column 21, line 1, please delete "," following the word engaging.

UNITED STATES PATENT AND TRADEMARK OFFICE
CERTIFICATE OF CORRECTION

| | | |
|---|---|---|
| PATENT NO. | : 8,760,508 B2 | Page 1 of 1 |
| APPLICATION NO. | : 12/686489 | |
| DATED | : June 24, 2014 | |
| INVENTOR(S) | : Brantley et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 628 days.

Signed and Sealed this
Twenty-first Day of July, 2015

Michelle K. Lee
*Director of the United States Patent and Trademark Office*